(12) United States Patent
Li et al.

(10) Patent No.: US 10,227,339 B2
(45) Date of Patent: Mar. 12, 2019

(54) SALT FORM AND CRYSTAL FORM OF 1,2,5-THIADIAZOLIDIN-1,1-DIOXIDE, PREPARATION METHOD THEREOF AND INTERMEDIATE

(71) Applicant: JIANGSU KANION PARMACEUTICAL CO. LTD, Lianyungang (CN)

(72) Inventors: Peng Li, Lianyungang (CN); Bailing Yang, Lianyungang (CN); Fei Hao, Lianyungang (CN); Zheng Wang, Lianyungang (CN); Zongbin Li, Lianyungang (CN); Haiying He, Lianyungang (CN); Shuhui Chen, Lianyungang (CN); Wei Xiao, Lianyungang (CN); Wang Shen, Lianyungang (CN); Zhenzhong Wang, Lianyungang (CN)

(73) Assignee: Jiangsu Kanion Pharmaceutical Co. Ltd, Lianyungang (CN)

( * ) Notice: Subject to any disclaimer, the term of this patent is extended or adjusted under 35 U.S.C. 154(b) by 0 days.

(21) Appl. No.: 15/573,061

(22) PCT Filed: Oct. 25, 2016

(86) PCT No.: PCT/CN2016/103297
§ 371 (c)(1),
(2) Date: Nov. 9, 2017

(87) PCT Pub. No.: WO2017/071569
PCT Pub. Date: May 4, 2017

(65) Prior Publication Data
US 2018/0141940 A1 May 24, 2018

(30) Foreign Application Priority Data

Oct. 26, 2015 (CN) .......................... 2015 1 0703726

(51) Int. Cl.
| C07D 417/14 | (2006.01) |
| C07D 213/87 | (2006.01) |
| C07D 401/04 | (2006.01) |
| C07D 417/04 | (2006.01) |
| C07B 41/02 | (2006.01) |
| C07B 43/04 | (2006.01) |

(52) U.S. Cl.
CPC ............ *C07D 417/14* (2013.01); *C07B 41/02* (2013.01); *C07B 43/04* (2013.01); *C07D 213/87* (2013.01); *C07D 401/04* (2013.01); *C07D 417/04* (2013.01); *C07B 2200/13* (2013.01)

(58) Field of Classification Search
CPC ..................................................... C07D 417/14
See application file for complete search history.

(56) References Cited

U.S. PATENT DOCUMENTS 9,988,361 B2 * 6/2018 Li ........................ C07D 417/04
2007/0049623 A1   3/2007 Chern
2017/0066732 A1 * 3/2017 Li ........................ C07D 417/04

FOREIGN PATENT DOCUMENTS

| CN | 1173131 | 2/1998 |
| CN | 100999441 | 7/2007 |
| CN | 103351352 | 10/2013 |
| CN | 105085512 | 11/2015 |
| WO | 2008142550 | 11/2008 |
| WO | WO-2015165340 A1 * 11/2015 ........... C07D 405/14 |

OTHER PUBLICATIONS

Prajapti, Santosh Kumar, "An efficient synthesis of 5-substituted 1H-tetrazoles via B(C6F5) 3-catalyzed [3+2] cycloaddition of nitriles and sodium azide", Tetrahedron Letters, vol. 55, Issue 24, Jun. 11, 2014, pp. 3507-3510.
Registry Copyright 2017, ACS on STN. "Reg No. 1312919-49-5", chemical Catalog; Supplier: TC Scientific Inc., Jul. 18, 2011.

\* cited by examiner

*Primary Examiner* — Nyeemah A Grazier
(74) *Attorney, Agent, or Firm* — Jason P. Mueller; Adams and Reese LLP (57) ABSTRACT

The present invention discloses a salt form, crystal form and intermediate of the compound 1, and preparation method thereof.

Compound 1

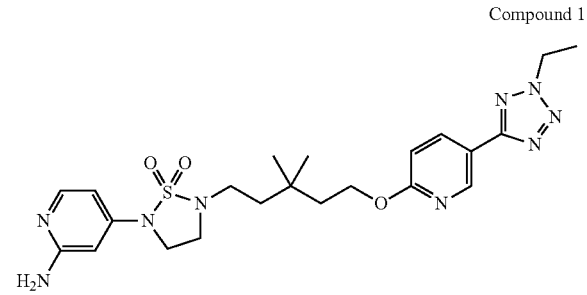

8 Claims, 3 Drawing Sheets

SALT FORM AND CRYSTAL FORM OF 1,2,5-THIADIAZOLIDIN-1,1-DIOXIDE, PREPARATION METHOD THEREOF AND INTERMEDIATE

FIELD OF TECHNOLOGY

The present invention relates to a salt form, crystal form and intermediate of the compound 1 and preparation method thereof.

BACKGROUND

The enterovirus 71 is a member of small RNA virus family and one of the most common etiologies of hand-foot-mouth disease. It can also cause various diseases related to nervous system such as herpes pharyngitis, aseptic meningitis, encephalitis, and poliomyelitis-like paralysis and is possibly accompanied with severe central nervous system complications or neuritic pulmonary edema.

The hand-foot-mouth disease has the features of strong epidemic intensity, strong infectivity, and complex transmission route. There is no specific anti-enterovirus 71 medicine yet.

Although the existing technologies such as the patents of US20030087936, U.S. Pat. No. 6,706,739, US20040116476, US20050267164, and US20070049623 have disclosed a series of structures, for example the structures represented by Formula (B-I), it is still needed in urgency to develop a novel compound with better activity which is more beneficial to make medicine.

(B-I)

SUMMARY

The present invention provides a preparation method of compound 1,

Compound 1 comprising the following steps:

wherein,
molar ratio of the compound 3-2 and the $NaNO_2$ is 1:1~2;
reaction solvent used in preparation of the compound 3-3 from the compound 3-2 is selected from methanol/water, ethanol/water, isopropanol/water or acetic acid/water;
volume ratio of the water and the methanol, the ethanol, the isopropanol or the acetic acid is 1:1~3;
weight ratio of the compound 3-2 and $H_2O$ is 1:1~3.

In some solutions according to the present invention, the above preparation method comprises the following steps:

wherein,
reaction solvent used in preparation of the compound 3-2 from the compound 3-1 is selected from methanol/dioxane, ethanol/dioxane, isopropanol/dioxane;
volume ratio of the dioxane and the methanol, the ethanol, or the isopropanol is 0.5~1:0.5~1; molar ratio of the compound 3-1 and the alkali A is 1:1~2;
the alkali A is selected from sodium methoxide, sodium ethoxide, potassium tert-butoxide, lithium tert-butoxide, sodium tert-butoxide, aluminium isopropoxide, sodium hydride, potassium hydride, calcium hydride, lithium hydroxide, sodium hydroxide, potassium hydroxide, cesium hydroxide, sodium carbonate, potassium carbonate, cesium carbonate, sodium hydrogen carbonate and/or potassium hydrogen carbonate;
molar ratio of the compound 3-1 and the hydrazine hydrate is 1:2~15.

In some solutions according to the present invention, the molar ratio of the compound 3-1 and the alkali A is 1:1.5;

In some solutions according to the present invention, the molar ratio of the compound 3-1 and the hydrazine hydrate is 1:6~9.

In some solutions according to the present invention, the above preparation method comprises the following steps:

wherein,
molar ratio of the 2-amino-4-bromopyridine and the compound 2-4 is 1:1~2;
molar ratio of the ligand and the compound 2-4 is 0.1~0.5:1;
the ligand is selected from TRANS-N,N'-dimethylcyclohexyl-1,2-diamine, N,N'-dimethylethanediamine or Xphos;
the catalyst is selected from CuI, $Pd_2(dba)_3$;
molar ratio of the alkali B and the compound 2-4 is 2~4:1;
the alkali B is selected from lithium hydroxide, sodium hydroxide, potassium hydroxide, cesium hydroxide, sodium carbonate, potassium carbonate, cesium carbonate, sodium hydrogen carbonate and/or potassium hydrogen carbonate;
reaction solvent used in preparation of the compound 2-5 from the compound 2-4 is selected from DMF, dioxane or dimethyl sulfoxide; weight ratio of the reaction solvent and the compound 2-4 is 10~20:1.

In some solutions according to the present invention, the molar ratio of the 2-amino-4-bromopyridine and the compound 2-4 is 1:1.5;

In some solutions according to the present invention, the molar ratio of the ligand and the compound 2-4 is 0.2:1.

In some solutions according to the present invention, the molar ratio of the alkali B and the compound 2-4 is 3:1.

In some solutions according to the present invention, the molar ratio of the reaction solvent and the compound 2-4 is 15:1.

In some solutions according to the present invention, the above preparation method comprises the following steps:

wherein,
the reductant is red-Al (red aluminum);
molar ratio of the compound 1-2 and the red-Al is 1:1~4;
In some solutions according to the present invention, the molar ratio of the compound 1-2 and the red-Al is 1:2~3;
In some solutions according to the present invention, the present invention further comprises the following step:

In some solutions according to the present invention, the present invention further comprises the following step:

In some solutions according to the present invention, the present invention further comprises the following step:

3-5

In some solutions according to the present invention, the present invention further comprises the following step:

In some solutions according to the present invention, the present invention further comprises the following step:

Compound 1

Figure 1:
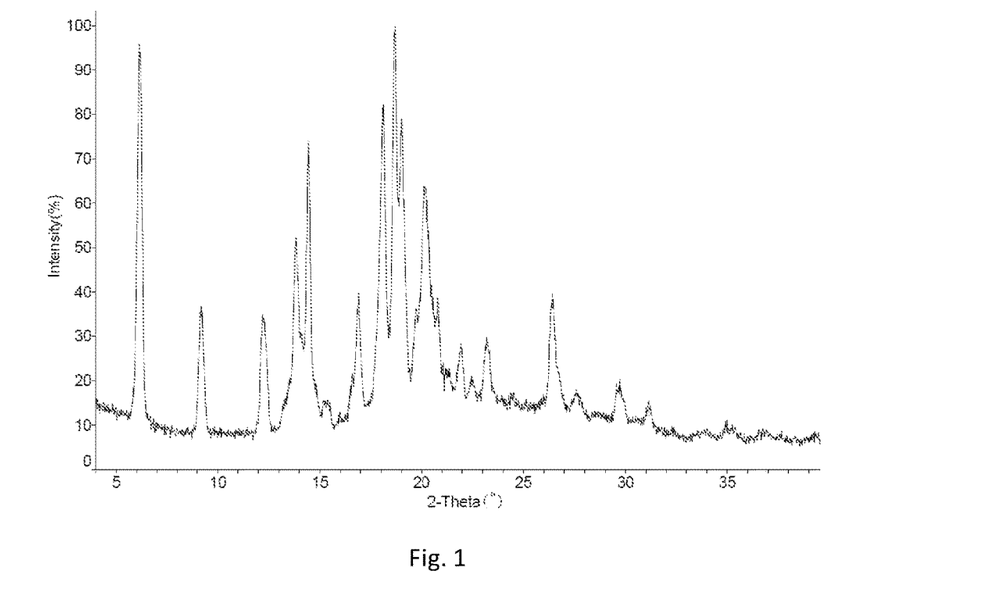
FIG. 1 shows the XRPD spectra of Cu-Kα radiation of crystal form A.
Figure 2:
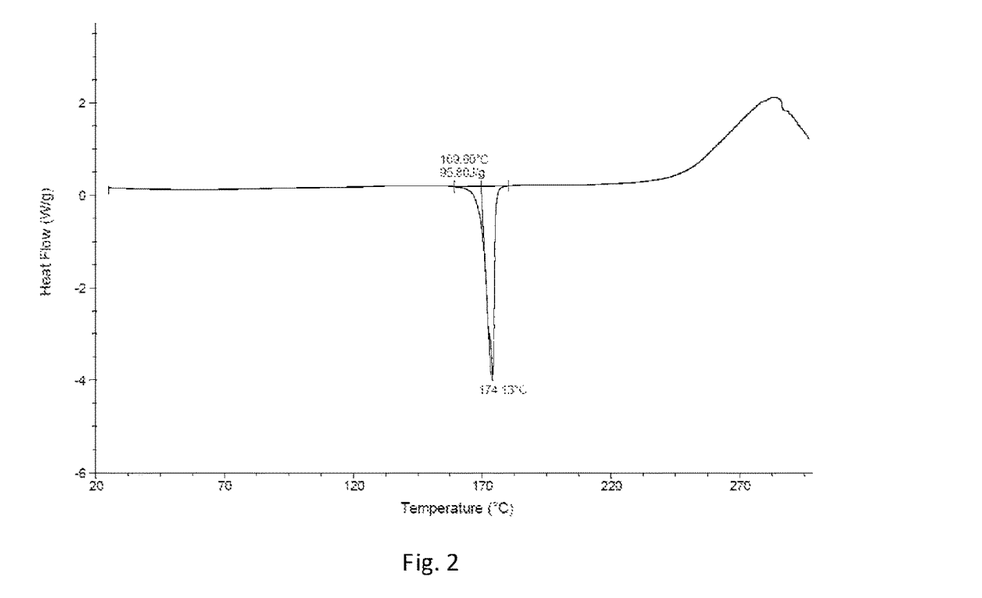
FIG. 2 shows the DSC spectra of crystal form A.
Figure 3:
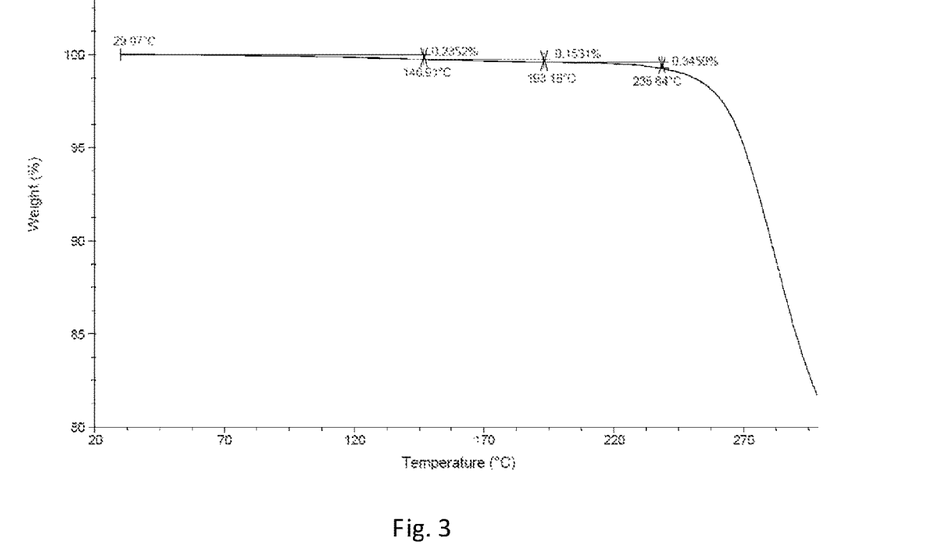
FIG. 3 shows the TGA spectra of crystal form A.

In some solutions according to the present invention, the present invention comprises the following step:

The present invention further provides the following compounds used as intermediate in preparation of the compound 1:

The present invention further provides crystal form A of the compound 1, and the XRPD spectrum of which is as shown in FIG. 1.

TABLE 1

| | XRPD spectral analysis data of crystal form A | | |
|---|---|---|---|
| NO. | 2-Theta | d(A) | I % |
| 1 | 6.151 | 14.3575 | 100.0 |
| 2 | 9.206 | 9.5988 | 34.0 |
| 3 | 12.205 | 7.2457 | 31.1 |
| 4 | 13.840 | 6.3931 | 46.2 |
| 5 | 14.452 | 6.1240 | 69.8 |
| 6 | 16.586 | 5.3404 | 9.4 |
| 7 | 16.916 | 5.2370 | 30.4 |
| 8 | 18.118 | 4.8921 | 79.6 |
| 9 | 18.690 | 4.7436 | 92.4 |
| 10 | 19.027 | 4.6605 | 63.0 |
| 11 | 19.718 | 4.4986 | 14.4 |
| 12 | 20.132 | 4.4071 | 50.1 |
| 13 | 20.809 | 4.2652 | 10.1 |
| 14 | 21.964 | 4.0434 | 11.3 |
| 15 | 22.476 | 3.9525 | 5.4 |
| 16 | 23.208 | 3.8294 | 16.5 |
| 17 | 26.422 | 3.3705 | 30.4 |
| 18 | 27.605 | 3.2287 | 5.8 |
| 19 | 29.714 | 3.0041 | 10.3 |
| 20 | 31.132 | 2.8704 | 5.9 |

The present invention further provides compound 2 represented by the following formula:

compound 2

Figure 4:
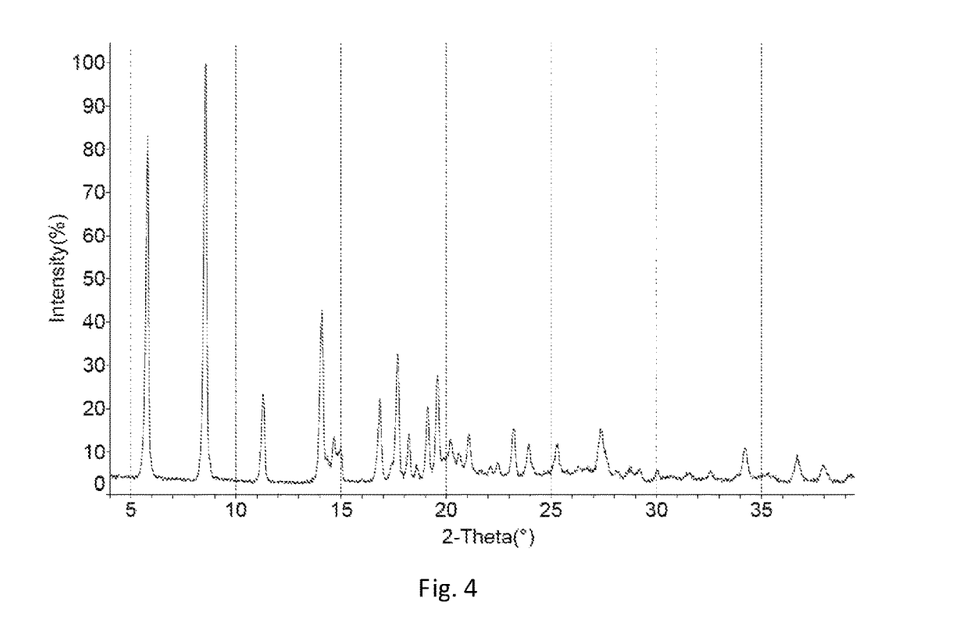
FIG. 4 shows the XRPD spectra of Cu-Kα radiation of crystal form B.
Figure 5:
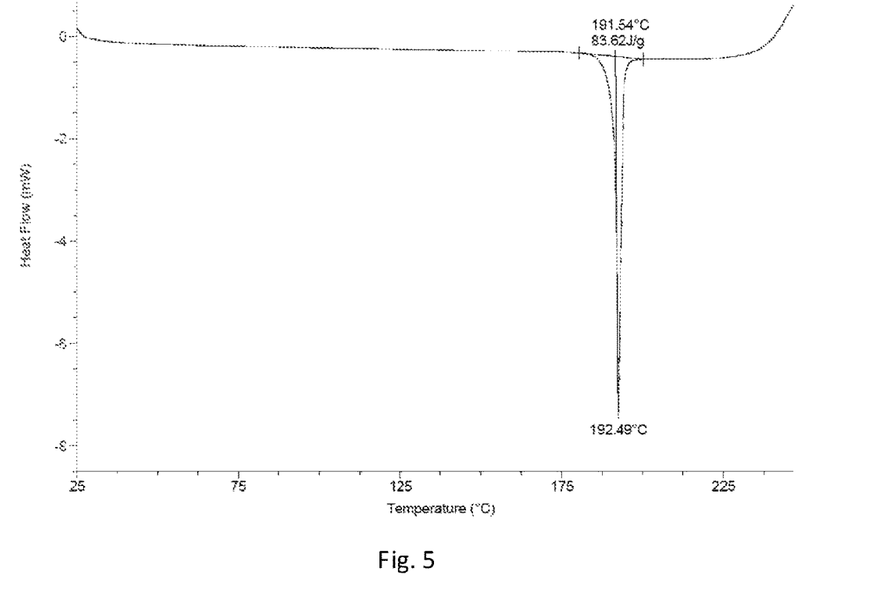
FIG. 5 shows the DSC spectra of crystal form B.
Figure 6:
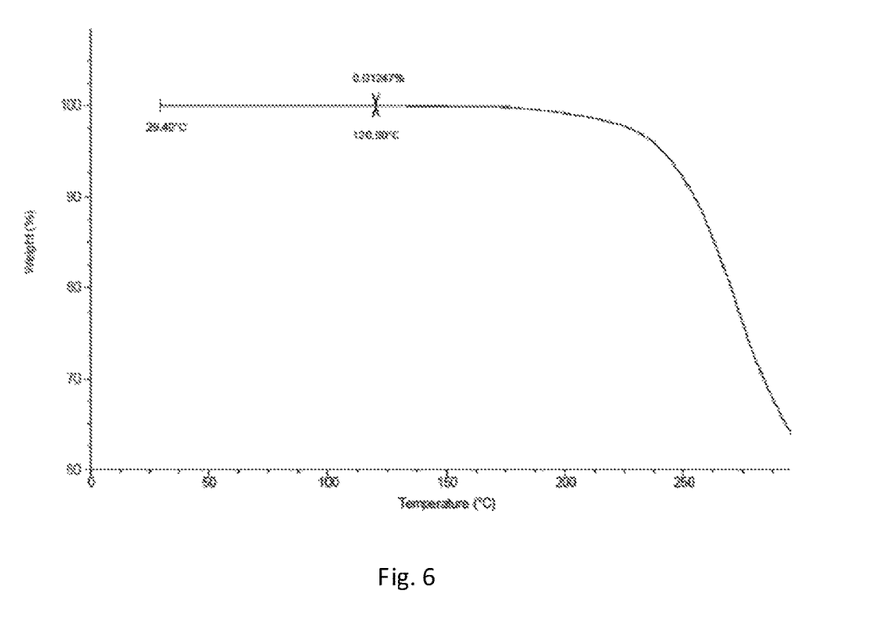
FIG. 6 shows the TGA spectra of crystal form B.

The present invention further provides crystal form B of the compound 2, and the XRPD spectrum of which is as shown in FIG. 4.

TABLE 2

XRPD spectral analysis data of crystal form B

| NO. | 2-Theta | d(A) | I % |
|---|---|---|---|
| 1 | 5.637 | 15.6641 | 84.0 |
| 2 | 8.397 | 10.5209 | 100.0 |
| 3 | 11.160 | 7.9216 | 18.0 |
| 4 | 13.937 | 6.3491 | 43.2 |
| 5 | 14.253 | 6.2088 | 37.6 |
| 6 | 14.513 | 6.0982 | 86.5 |
| 7 | 14.846 | 5.9622 | 68.1 |
| 8 | 16.701 | 5.3041 | 58.4 |
| 9 | 17.272 | 5.1299 | 16.3 |
| 10 | 17.549 | 5.0496 | 97.7 |
| 11 | 18.099 | 4.8972 | 45.8 |
| 12 | 18.444 | 4.8065 | 7.0 |
| 13 | 18.987 | 4.6702 | 61.0 |
| 14 | 19.443 | 4.5617 | 69.6 |
| 15 | 20.094 | 4.4152 | 59.5 |
| 16 | 20.469 | 4.3353 | 32.3 |
| 17 | 20.959 | 4.2349 | 28.6 |
| 18 | 22.000 | 4.0369 | 4.8 |
| 19 | 22.284 | 3.9861 | 6.3 |
| 20 | 23.071 | 3.8519 | 30.6 |
| 21 | 23.820 | 3.7325 | 21.7 |
| 22 | 25.234 | 3.5263 | 6.4 |
| 23 | 26.545 | 3.3551 | 3.7 |
| 24 | 27.233 | 3.2719 | 62.9 |
| 25 | 28.595 | 3.1191 | 5.6 |
| 26 | 29.105 | 3.0656 | 8.4 |
| 27 | 29.899 | 2.9859 | 3.7 |
| 28 | 30.604 | 2.9188 | 6.9 |
| 29 | 31.413 | 2.8454 | 9.2 |
| 30 | 32.416 | 2.7597 | 3.5 |
| 31 | 34.094 | 2.6276 | 10.2 |
| 32 | 34.806 | 2.5754 | 5.7 |
| 33 | 36.520 | 2.4583 | 8.0 |
| 34 | 37.860 | 2.3744 | 5.0 |

The present invention provides a preparation method of crystal form B, comprising: dissolve any form of the compound 1 in the mixed solvent of DMF and acetone, and drop DMF solution of hydrogen chloride into the mixed solvent under stirring conditions. After the dropping is completed, slowly add acetic ether and crystal form B is obtained after crystallization.
wherein, weight ratio of the compound 1 and the DMF is 1:5~10;
volume ratio of the DMF and the acetone is 4~6:1;
volume ratio of the DMF and the acetic ether is 1:1~4;
In some solutions according to the present invention, the volume ratio of DMF and acetone is 5:1.
In some solutions according to the present invention, the volume ratio of the DMF and the acetic ether is 1:2~3.
Another purpose of the present invention is providing a use of crystal form A of the compound 1 and crystal form B of the compound 2 in preparing drugs for treatment of diseases associated with the enterovirus 71.

Definitions and Descriptions

Unless indicated otherwise, the following terms and phrases used here are intended to have the following meanings. Any specific term or phrase without specific definition should not be regarded as uncertain or indistinctive but should be understood as its common meaning. Any trade name appearing in the present invention denotes the corresponding product it refers to or its active ingredient.

The intermediate compound(s) according to the present invention can be prepared via many synthesis methods known by those skilled in the art, which include the following embodiments, the implementation ways formed by them with other chemical synthesis methods and the equivalent replacements known by those skilled in the art. The preferred embodiments include but are not limited to the examples according to the present invention.

The chemical reaction of the embodiment according to the present invention is accomplished in a suitable solvent, which must be adapted to the chemical changes of the invention and the reagents and materials required. In order to obtain the compounds of the present invention, sometimes it is necessary for those skilled in the art to modify or select the synthetic steps or reaction processes on the basis of the existed implementation methods.

An important consideration in any synthetic route in this field is to select the appropriate protective group for reactive functional groups (such as the amino group in the present invention). For trained practitioners, Greene and Wuts (Protective In Organic Synthesis, Wiley and Sons, 1991) is an authority in this filed. All references cited in the invention are integrally incorporated into the present invention.

The present invention will be described through the embodiments in detail below, and these embodiments do not imply any limitation to the present invention.

All the solvents used in the present invention are commercially available and can be used directly without further purification. The reaction is carried out under inert nitrogen and in anhydrous solvent. Proton NMR data are recorded in the Bruker Avance III 400 (400 MHz) spectrometer, the chemical shift is represented by a low field (PPM) of four methyl silane. Mass spectrometry was measured on Agilent 1200 series plus 6110 (&1956A). LC/MS or Shimadzu MS contains a DAD:SPD-M20A (LC) and Shimadzu Micromass 2020 detector. Mass spectrometer is equipped with electrospray ionization (ESI) operated in a positive or negative mode.

The present invention employs the following abbreviations: DCM denoting dichloromethane; PE denoting petroleum ether; EA denoting ethyl acetate; DMF denoting N,N-dimethylformamide; DMSO denoting dimethyl sulfoxide; EtOAc denoting ethyl acetate; EtOH denoting ethanol; MeOH denoting methanol; HCl (g) denoting hydrogen chloride gas; HOAc denoting acetic acid; TFA denoting trifluoroacetic acid; DIPEA denoting diisopropyl ethylamine; t-BuOK denoting potassium tert-butoxide; $PPh_3$ denoting triphenylphosphine; $Pd_2(DBA)_3$ denoting tri(dibenzalacetone) dipalladium; $Pd(PPh_3)_4$ denoting tetra(triphenylphosphine) palladium; $Pd(dppf)Cl_2$ denoting 1,1'-bis(diphenylphosphine) ferrocene palladium chloride; $Pd(PPh_3)_2Cl_2$ denoting dichloro bis(triphenylphosphine) palladium(II); $Pd(OAc)_2$ denoting palladium acetate; $PdCl_2$ denoting palladium chloride; CuI denoting cuprous iodide; CuBr denoting cuprous bromide; CuCl denoting cuprous chloride;

Cu₂O denoting cuprous oxide; Xantphos denoting 4,5-bis(diphenylphosphine)-9,9-dimethylxanthene; Sphos denoting 2-dicyclohexylphosphinidene-2',6'-dimethoxy biphenyl; Xphos denoting 2-dicyclohexylphosphino-2',4',6'-triisopropylbiphenyl; Ruphos denoting 2-bicyclohexyl phosphine-2',6'-diisopropoxy-1,1'-biphenyl; Brettphos denoting 2-(dicyclohexyl phosphino)-3,6-dimethoxy-2'-4'-6'-triisopropyl biphenyl-1,1'-biphenyl; MSCI denoting methylsufonyl chloride; $NH_2NH_2 \cdot H_2O$ denoting hydrazine hydrate; $SOCl_2$ denoting sulfoxide chloride; $CDCl_3$ denoting deuterated chloroform.

The compound(s) is(are) named manually or via ChemDraw® software. The commercially-available compounds are used with the names from supplier directory.

Process for synthesis of the compounds 1 and intermediates thereof according the present invention has the beneficial effect as following: the raw materials are cheap and easy to get, and the process has overcome the disadvantages of the reagents used having poison, harsh reaction condition, difficulties in separation, purification and industrialization.

Specifically:

1) Regarding preparation of the compound 1-3, $LiAlH_4$ and borane are used for reduction of ester group in the existing technology. When using the $LiAlH_4$, the reaction is acute and flammable, and thus making against the amplification of the reaction. The borane is flammable and smelly, and thus increasing the operation difficulties in the process. The present invention uses liquid Red-Al, and the reaction has the advantages of simplicity of operation, mildness and quantitative conversion;

2) Regarding preparation of the compound 2-5, Ullman reaction is used for the first time to achieve the coupling of 4-bromine-2-amino pyridine and sulfonylurea, and column purification is not required in post-processing;

3) Regarding preparation of the compound 3-3, synthesis method needs protection, and a new method is used in the synthesis of tetrazole fragment. The method has the advantages of simplicity of operation, easily amplification, and thus replacing the traditional sodium azide which is highly toxic and explosive.

Therefore, the invention has great industrial application value and economic value in preparation of the compounds (I) and intermediates thereof.

X-Ray Powder Diffractometer (XRPD) Method of the Present Invention

Instrument type: Brook D8 advance X-ray diffractometer

Test conditions: detailed XRPD parameters are as follows:

X-ray generator: Cu, Kα (λ=1.54056 Å)
Tube voltage: 40 kV, tube current: 40 mA
Emission slit: 1 deg
Limited height slit: 10 mm
Scattering slit: 1 deg
Accept slit: 0.15 mm
Monochromator: fixed monochromator
Scan range: 4-40 deg
Scanning speed: 10 deg/min Differential Scanning Calorimeter (DSC) Method of the Present Invention Instrument type: TA Q2000 differential scanning calorimeter Test conditions: samples (~1 mg) are placed in the DSC aluminum pan, test method: 25° C.~250° C. or 300° C., and the heating rate is 10° C./min.

Thermal Gravimetric Analyzer (TGA) Method of the Present Invention

Instrument type: TA Q5000IR thermogravimetric analyzer

Test conditions: samples (2~5 mg) are placed in TGA platinum pot, test method: room temperature –300° C., and the heating rate is 10° C./min.

DETAILED DESCRIPTION

In order to understand the present invention better, the following examples are provided to further describe although the scope of the present invention is not limited to them.

Example 1: Preparation of the Compound 1-3

Process 1:

Step 1: Preparation of the Compound 1-2

Dissolve the compound 1-1 (5.0 kg) into EtOH (20 L), then slowly add $SOCl_2$ (486 mL) into the solution under the temperature of 0-25° C. ( ) After the adding, slowly heat the mixture to 80° C. and agitate it for 12 hours. After the reaction, the solvent of the mixture is removed under reduced pressure condition, then wash the residue with saturated sodium carbonate solution (1 L) and extract the solution with ethyl acetate (5 L) for 3 times. Wash the combined organic phase with saturated salt water (1 L), then dry the extraction with anhydrous sodium sulfate. After filtration, concentrate the filtrate to obtain the compound 1-2 (yellow oil, 6.75 kg, 100%) which can be directly used in the next step.

Step 2: Preparation of the Compound 1-3

In reactor, dissolve the compound 1-2 (2.0 kg, 9.25 mol) into anhydrous toluene (12 L) and keep the temperature below 25° C. After slowly dropping the red-Al (8.00 kg, 8.00 L, 25.98 mol, 65%) into the solution, heat the mixture to 15°

C. slowly and agitate it for 19 hours. Stop stirring, slowly add the reaction mixture into ice water system (10 L) and stir it vigorously. Then add sodium hydroxide (500 g×8) in batches into the mixed system and supplementary ice water (6 L) is also added. After the aqueous phase of the system becomes transparent from the turbidity, separate the toluene phase of upper layer and extract the remaining mixed phase with methyl tert butanol ether (10 L×2, 5 L×1), then dry the extraction with anhydrous sodium sulfate. After filtration, concentrate the filtrate to obtain the compound 1-3 (yellow oil, 1.17 kg, 96%). $^1$HNMR (CDCl$_3$, 400 MHz) δ3.69 (m, 4H), 1.55 (t, J=7.2 Hz, 4H), 0.93 (s, 6H).

Process 2: Preparation of the Compound 2-6

Step 3: Preparation of the Compound 2-3

Add the dried DCM (10 L) and the compound 2-1 (4.2 kg, 30 mol) into reactor. Keep the temperature below −10° C. and slowly drop tert butyl alcohol (2.3 kg, 31.5 mol) into the mixture in 4 hours. Then the compound 2-2 (3.5 kg, 30.6 mol) is added at one time. Slowly add triethylamine (10 kg, 100 mol, 14 L) (dropping in 8 hours) into the reactor below −10° C. After addition, keep the reaction liquid at about 5° C. and stir it for 60 hours. Then divide the reaction liquid into three parts. Add 10 L water into one part, and adjust the solution to pH 3~4 with 4N HCl, then a large number of white solids appear. After stirring and standing the solution to settle the solids, pump most of water away, and add 10 L water into the residue continually. Pump the water away after stirring and standing the solution, and add 10 L EA into the residue, then white solid is obtained after vacuum filtration. After the liquid stratification, dry the lower organic phase with anhydrous sodium sulfate and then evaporate it to obtain pale yellow solid. The pale yellow solid is recrystallized with ethyl acetate/n-heptane=1 L/1 L to obtain compound 2-3 (1.4 kg). The other two parts are dealt with the same way and the compound 2-3 (white solid, 4.9 kg, 64%) are obtained after drying. $^1$HNMR (d-DMSO, 400 MHz) δ 7.90-7.88 (m, 1H), 3.64-3.61 (m, 2H), 3.25-3.20 (m, 2H), 1.43 (s, 9H).

Step 4: Preparation of the Compound 2-4

Add DMSO (20 L) and the compound 2-3(2 kg, 7.8 mol) into reactor and keep the temperature at 19° C. Then add K$_2$CO$_3$(1.6 kg, 11.6 mol) into the reactor and keep the temperature of the mixture at 18-25° C. for 17 h. Samples are tested during the reaction to control the extent of reaction until TLC (PE:EA=1:1) has shown the completion of the reaction. After standing and layering the reaction solution, wash the lower solid 3 times with DMSO (1 L×3) and combine the up clear liquid and DMSO phase, then the mixture liquid is divided into two parts. Add 30 L water into one part, and adjust the solution to pH 3~4 with 5N HCl, then a large number of white solids appear. The white solid is obtained after vacuum filtration. Add ethyl acetate/n-heptane (1:5) into the white solids and agitate the mixture solution. Filter the above solution and dry the filtrates under vacuum to obtain the compound 2-4 (white solid, 1.4 kg, 81%). $^1$HNMR (d-DMSO, 400 MHz) δ 7.76-7.70 (m, 1H), 3.75-3.72 (m, 2H), 3.37-3.32 (m, 2H), 1.40 (s, 9H).

Step 5: Preparation of the Compound 2-5

Under the protection of N$_2$ gas, add DMF (8 L) into 30 L reactor, then add the compound 2-4 (500 g, 2.89 mol), 2-amino-2-bromopyridine (963.5 g, 4.33 mol), TRANS-N,N'-dimethylcyclohexyl-1,2-diamine (82.2 g, 0.578 mol), CuI (824.6 g, 4.33 mol) and K$_2$CO$_3$ (1.2 Kg, 8.67 mol) into the reactor. Under the protection of N$_2$ gas, keep the temperature of the mixture at 80° C. for 17 h. Samples are tested during the reaction until the result has shown disappearance of raw material, then cool the reactor to 10° C. and divide the mixture liquid into two parts. Add 20 L water and 2.5 L ammonia into one part and agitate it for 50 min. Keep the temperature of the reactor at 10° C., then filter the mixture liquid and wash the filtrated solid with 1 L water. After vacuum filtration, add the filtrated solid to the reactor containing 5 L ethyl acetate, then add acetic acid (750 mL) to dissolve the solid (the solution is blue-black). Dilute 1.25 L ammonia with 1 L water and then drop it into the reactor, and keep the temperature of the reactor below 20° C. After addition, filter the mixture liquid and wash the solid to obtain the crude compound 2-5 (pale yellow solid, 660 g, 67%). $^1$H NMR (d-DMSO, 400 MHz) δ 7.87-7.86 (m, 1H), 6.40-6.39 (m, 1H), 6.30 (s, 1H), 6.09 (s, 2H), 3.98-3.92 (m, 2H), 3.84-3.81 (m, 2H).

Step 6: Preparation of the Compound 2-6

Add dioxane hydrochloride solution (4N, 16 L) into reactor and then add the compound 2-5(916 g, 2.91 mol) in batches. After addition, agitate the mixture at 45° C. for 18 h. After sampling test has shown disappearance of raw material, cool the reaction system to 25° C., and add 15 L tert-Butyl methyl ether, then agitate the mixture liquid for 15 min to obtain large amounts of white solids. Filter the solids under vacuum to obtain the compound 2-6 (white solid, 730 g, 100%), $^1$HNMR (d-DMSO, 400 MHz) δ 13.5 (m, 1H), 8.57-8.54 (m, 1H), 7.93-7.92 (m, 2H), 6.64-6.61 (m, 1H), 6.43 (s, 1H), 3.95-3.92 (m, 2H), 3.60-3.56 (m, 2H).

Process 3: Preparation of the Compound 2

Compound 2

Step 7: Preparation of the Compound 3-2

Under the protection of $N_2$ gas, add dried methanol (12.5 L), dioxane (12.5 L) and the compound 3-1 (5 kg, 36 mol) into 50 L reactor, cool the temperature outside to 0° C., keep the temperature inside at 0-3° C. and slowly drop sodium methoxide (390 g, 2 L methanol solvent, 7.2 mol) into the reactor in 1 h. Keep the temperature inside at 0-5° C. for 1.5 h, then heat the mixture solution to 20° C. and maintain for 0.5 h. Slowly add hydrazine hydrate (1875 mL, 38.6 mol) into the reactor and keep the temperature inside at 20-30° C. for 1 h, then the white solid is precipitated from the solution. Add 12.5 L tert-Butyl methyl ether into the solution, then agitate it for 0.5 h and cool it to 10° C. After filtration, the compound 3-2(4.3 kg, 70%) is obtained. $^1$HNMR (DMSO-d6, 400 MHz) δ 8.69-8.68 (m, 1H), 8.09-8.07 (m, 1H), 7.49-7.47 (m, 1H), 5.81 (s, br, 2H), 5.25 (s, br, 2H).

Step 8: Preparation of the Compound 3-3

Under the protection of $N_2$ gas, add acetic acid (9 L), water (7.2 L) and the compound 3-2 (3 kg, 17.58 mol) into 30 L reactor, keep the temperature inside at 20-30° C. and slowly drop sodium nitrite (1.46 kg, dissolved in 3 L water, 21.1 mol) into the reactor within 1.5 h. The reaction mixture is maintained for 1 h at room temperature 20° C., then large amounts of yellow solids are precipitated from the solution. Add 9 L water into the reactor and cool it to 0-5° C., then adjust the solution to PH 2 with 6H HCL (3 L). The reaction solution is filtrated to obtain the yellow solid, then wash the residue with 1 L cold tert-Butyl methyl ether and dry it under vacuum to obtain yellow solid compound 3-3 (2.68 kg, 84%). $^1$HNMR (DMSO-d6, 400 MHz) δ 9.05 (m, 1H), 8.45-8.43 (m, 1H), 7.81-7.79 (m, 1H).

Step 9: Preparation of the Compound 3-4

Add the compound 3-3 (1.02 kg, 5.62 mol) and DMF (5.6 L) into reactor. Keep the reaction temperature at 10-20° C. and add potassium carbonate (1.55 kg, 11.24 mol) into the reactor. Then keep the temperature below 20° C. and add bromoethane (919 g, 8.43 mol) into the reactor. The reaction is maintained at 40° C. for 4 h. After cooling the reaction mixture to 20° C., add 10 L water and agitate the mixture solution for 30 min. Filtrate the white suspension and wash the residue with water (1 L×2) and n-heptane (1 L×2) for 2 times. Dry the residue under vacuum to obtain the compound 3-4 (pale yellow solid, 1.15 kg, 89.3%). $^1$HNMR (DMSO-d6, 400 MHz) δ 9.17 (m, 1H), 8.42-8.39 (m, 1H), 7.50-7.48 (m, 1H), 4.76 (q, J=7.2 Hz, 2H), 1.73 (t, J=7.2 Hz, 3H).

Step 10: Preparation of the Compound 3-5

Keep the reactor at 25° C. under the protection of $N_2$ gas, then add the compound 3-4(1.14 kg, 5.0 mol, content:

91.6%), the compound 1-3 (2.0 kg, 15 mol) and DMF (10.9 L) into 30 L reactor. Then keep the temperature inside below 30° C. and add cesium carbonate (4.89 kg, 15 mol) into the reactor. Stir the mixture at 70° C. to react for 20 h until the LCMS has shown disappearance of raw material A. After cooling the reaction liquid to room temperature, add 17 L water and 20 L dichloromethane into the reaction liquid, and then agitate it for 10 min. After standing and layering, wash the organic layer with water (15 L×2) for 2 times and dry it with anhydrous sodium sulfate, then filtrate and dry the mixture liquid to obtain the crude compound 3-5 (pale yellow oily liquid, 2.40 kg, 94.1%). Purity, detected by LCMS, is 77.3%. $^1$HNMR (DMSO-d6, 400 MHz) δ 8.91 (s, 1H), 8.30-8.26 (m, 1H), 6.85-6.81 (m, 1H), 4.70 (q, J=7.2 Hz, 2H), 4.44 (t, J=7.6 Hz, 3H), 3.77 (t, J=7.6 Hz, 3H), 1.78 (t, J=7.2 Hz, 3H), 1.70-1.62 (m, 4H), 1.02 (s, 6H).

Step 11: Preparation of the Compound 3-6

Under the protection of $N_2$ gas, add the compound 3-5 (1.97 kg, 3.62 mol, content: 56.1%), DIPEA (936 g, 5.43 mol) and dichloromethane (12 L) into 30 L reactor, agitate the mixture for 5 min at 0-5° C., then slowly add methane sulfonyl chloride (598.15 g, 5.43 mol) into the mixture to react for 1 h at 5° C. until the LCMS has shown disappearance of raw material 3-5. Add 16 L water into the reactor, and agitate it for 10 min. After standing and layering, the water layer is extracted by dichloromethane (4 L). The organic layer are combined and washed with 16 L water, and then dried with anhydrous sodium sulfate. After filtration, the solution is dried under vacuum to obtain the compound 3-6 (brown oily liquid, 1.45 kg, 84.5%). $^1$H NMR (CDCl3, 400 MHz) 8.92 (d, J=2.0 Hz, 1H), 8.27 (dd, J=8.5, 2.0 Hz, 1H), 6.83 (d, J=9.0 Hz, 1H), 4.66-4.73 (m, 2H), 4.44 (t, J=7.0 Hz, 2H), 4.37 (t, J=7.3 Hz, 2H), 3.02 (s, 3H), 1.80 (dt, J=14.2, 7.2 Hz, 4H), 1.69 (t, J=7.5 Hz, 3H), 1.06 (s, 6H).

Step 12: Preparation of the Compound 1

Under the protection of $N_2$ gas, add the compound 3-6 (2.04 kg, 5.31 mol, content: 81%), the compound 2-6 (1.3 kg, 5.18 mol), cesium carbonate (7.03 kg, 21.57 mol), potassium iodide (716.21 g, 4.31 mol) and DMF (30 L) into 50 L jacketed bottle, mechanically agitate the mixture for 16 h at 65° C. Cool the reaction liquid to 20° C. and divide it into 3 parts equally. Add 20 L water into the reacting bottle, slowly pour ⅓ of the reaction liquid into the bottle in stirring condition. After large amounts of solid is precipitated from the solution, agitate the solution and cool it to 10° C. Filtrate the white suspension and wash the residue with 2 L water. Non viscous solid can be got after suction filtration and finally yellow crude solid is obtained. The remained ⅔ reaction liquid is dealt with the same method as above. 5 kg creamy-white wet solids are obtained finally. The wet solids (5 kg, 9.97 mol) are divided into 3 parts and ⅓ of them are dissolved in DMF (6 L) at 50-60° C. Slowly pour the above solution into 20 L pure water under mechanical agitation, then cool the mixture solution to 10-15° C. and filtrate it through suction filtration. Wash the residue with 2 L water. Non viscous solid can be got after suction filtration and finally yellow crude solid is obtained. The remained ⅔ solids are dealt with the same method as above in batches. 4.6 kg crude products (except inorganic salt) are obtained finally. The obtained solids are dealt with the same method as above again. 4.2 kg crude products (except inorganic salt) are obtained finally. The above 4.2 kg solids are suspended in 30 L acetone and the solution is heated to reflux until most of the solids are dissolved. Then cool it to 40° C. and spread 500 g diatomite to filtrate the solution. The filtration is dried under vacuum to obtain 3.5 kg crude products (except water). The above solids are dealt with the same operation as above again (25 L acetone). Filtrate the suspension and the filtrated solution is dried under vacuum to obtain 3 kg crude products. The above 3 kg solids are suspended in 12 L methyl tert butyl ether and agitate it at 60° C. in 2 h. Cool the mixed solution to 10-15° C., then filtrate it, wash the residue with 1 L methyl tert butyl ether, and dry the residue under suction filtration to obtain yellow crude solid (1.5 kg). The above 1.5 kg solids are divided into 3 parts and ⅓ of them (500 g) are dissolved in dichloromethane/methanol (10:1.10 L). Mix the sample solution and 4.5 kg neutral alumina and dry them under vacuum, then introduce sample in chromatography column, elute the sample with dichloromethane/methanol (10:1, 35 L). The remained ⅔ solids are dealt with the same method as above in batches. Then the above filtrated solution are combined and dried under vacuum to obtain the title compound 1 (pale yellow solid, crystal form A, 1.2 kg, 53%). LCMS (ESI) theoretical value [M+H]+: 501, measured value: 501. $^1$H NMR (CDCl3, 400 MHz), 8.93 (d, J=2.0 Hz, 1H), 8.28 (dd, J=8.8, 2.3 Hz, 1H), 7.97 (d, J=6.0 Hz, 1H), 6.85 (d, J=8.5 Hz, 1H), 6.43 (dd, J=5.8, 2.3 Hz, 1H), 6.30 (d, J=2.0 Hz, 1H), 4.71 (q, J=7.4 Hz, 2H), 4.58 (br. s., 2H), 4.45 (t, J=7.0 Hz, 2H), 3.81 (t, J=6.5 Hz, 2H), 3.50-3.56 (m, 2H), 3.24 (d, J=8.5 Hz, 2H), 1.81 (t, J=7.0 Hz, 2H), 1.74 (d, J=8.5 Hz, 2H), 1.67-1.71 (m, 3H), 1.08 (s, 6H).

STEP 13: Preparation of the Compound 2

Dissolve the compound 1(1.2 kg, 2.39 mol) in mixed solution of DMF (10.0 L) and acetone (2.0 L). Drop DMF containing HCL (2.75M, 957 mL) into the above solution under stirring (speed:150) to react for 2 h at 25° C. Slow down the stirring speed to 50, drop ethyl acetate (about 6 L) until minute quantities of solids are precipitated from the solution. Stop dropping, then agitate the solution to react for 1 h. Continue to drop ethyl acetate (6 L), then slowly add 12 L ethyl acetate into the solution and agitate the solution to react for 1 h at 25° C. Filtrate the solution, wash the residue with ethyl acetate (2 L×3), and dry the residue under suction filtration to obtain white solids (1.2 kg). Add the above 1.2 kg solids into ethyl acetate (6 L), heat the mixed solution to 40° C., and react for 3 h under stirring. Filtrate the solution, wash the residue with ethyl acetate (1.5 L×3), and dry the residue under suction filtration to obtain white solids (875 g). Dry the above 875 g solids at 45° C. for 16 h by vacuum drying oven to obtain white solids 870 g (830 g after micronization). Dissolve the compound 2 (825 g, 1.53 mol) in anhydrous DMF (8.25 L) to obtain pale yellow turbid solution in which a large of undissolved substances are suspended since the solids can not be completely dissolved in DMF. Directly filtrate the solution by G5 sand core funnel (3 L) at 25° C. in batches to obtain pale yellow clean solution (8.25 L). Add the compound 2 (815 g, dissolved in DMF (8.25 L)) and acetone (1.4 L) into 50 L reactor at 25° C. Adjust the stirring speed to 50, drop ethyl acetate (8 L) until minute quantities of solids are precipitated from the solution. Stop dropping, then agitate the solution to react for 1 h. Continue to drop 8 L ethyl acetate, then slowly add 24 L ethyl acetate into the solution and agitate the solution to react for 1 h at 25° C. Filtrate the solution, wash the residue with ethyl acetate (2 L×3), and dry the residue under suction filtration to obtain white solids (750 g), namely, crystal form B of compound 2. Add the above 750 g solids into ethyl acetate (3.5 L), heat the mixed solution to 40° C., and react for 3 h under stirring. Filtrate the solution, wash the residue with ethyl acetate (2 L×3), and dry the residue under suction filtration to obtain white solids (610 g). Dry the above 610 g solids at 45° C. for 16 h by vacuum drying oven to obtain the compound 2 (white solid, crystal form B, 595 g, 46%). The compound 2 is micronized to obtain white solid 584 g. LCMS (ESI) theoretical value [M+H]+: 501, measured value: 501. $^1$H NMR (d6-DMSO, 400 MHz), 13.3 (s, br, 1H), 8.84 (s, br, 1H), 8.30-8.20 (m, 1H), 8.00-7.85 (m, 3H), 7.00-6.95 (m, 1H), 6.70-6.60 (m, 1H), 6.50-6.45 (m, 1H), 4.77 (t, J=7.2 Hz, 2H), 4.42 (t, J=7.2 Hz, 2H), 3.99 (t, J=6.4 Hz, 2H), 3.65 (t, J=6.4 Hz, 2H), 3.20 (t, J=8.0 Hz, 2H), 1.74 (t, J=7.2 Hz, 2H), 1.69-1.66 (m, 2H), 1.58 (t, J=7.2 Hz, 3H), 1.01 (s, 6H).

Solubility Test of Crystal Form a in Different Solvents

Add 1~1.5 mg crystal form A of the compound 1 in volumetric flask, then single solvent or mixed solvent is added into the flask with multiple times until the solution become clear or solid particles disappear. The solubility of crystal form A in different solvents is determined thereby. The results are shown as table 3.

TABLE 3

Solubility of crystal form A in different solvents

| No. | Solvent | Solubility (mg/mL) |
|---|---|---|
| 1 | methanol | <1.98 |
| 2 | ethanol | <2.09 |
| 3 | acetone | 5.58-7.43 |
| 4 | ethyl acetate | <2.13 |
| 5 | 2-Methyltetrahydrofuran | <2.18 |
| 6 | 1,4-dioxane | 11.8-13.2 |
| 7 | Methanol-water (3:1) | <2.07 |
| 8 | Ethanol-water (3:1) | <2.32 |
| 9 | Acetone-water (3:1) | <2.24 |

Solubility Test of Crystal Form B in Different Solvents

Add 1~1.5 mg crystal form B of the compound 2 in volumetric flask, then single solvent or mixed solvent is added into the flask with multiple times until the solution become clear or solid particles disappear. The solubility of crystal form B in different solvents is determined thereby. The results are shown as table 4.

TABLE 4

Solubility of crystal form B in different solvents

| | | Solubility (mg/mL) | |
|---|---|---|---|
| No. | Solvent | 4 h | 24 h |
| 1 | 0.1N HCl | >872.73 | >935.05 |
| 2 | 0.01N HCl | >997.71 | >986.44 |
| 3 | pH 3.5 buffer solution | 232.28 | 185.63 |
| 4 | pH 4.5 buffer solution | 6.12 | 4.54 |
| 5 | pH 5.5 buffer solution | <0.10 | <0.10 |
| 6 | pH 6.5 buffer solution | <0.10 | <0.10 |
| 7 | pH 7.5 buffer solution | <0.10 | <0.10 |
| 8 | pH 6.8 buffer solution | <0.10 | <0.10 |
| 9 | water | 416.01 | 346.15 |
| 10 | normal saline | 42.87 | 43.43 |

Activity Evaluation In Vitro

Experimental 1: Test of EV71 In-Vitro Cytopathic Effect (CPE)

Purpose of Experiment:

To test the in-vitro antiviral activity and cytotoxicity of a compound to HFMD virus EV71 by means of cytopathic effect (CPE) test.

Test Materials:
1. Virus strain: Shenzhen/120F1/09
2. Cell line: RD cells of human rhabdomyoma
3. Cell culture media: DMEM medium added with 10% serum, Penicillin/Streptomycin and L-Glutannine (1×)
4. Test reagent: cellular activity test reagent CCK8

Test Method:
1. Cell inoculation: digest off the RD cells from the attached state, then dilute them with culture medium to a density of 80000/ml and inoculate 100 μl into the micro wells of the 96-well plate.
2. Dilution of Compound:
Step 1: prepare the dry powder of a compound to be tested into a 10 mM solution in DMSO. Then dilute the compound by three times to eight concentration points. Dilute the reference compounds with the same method.
Step 2: further dilute the diluted solution of the compound in DMSO with cell culture medium. Add 10 μl DMSO solution for each well into 240 μl culture medium.
3. Add the diluted compound solution by 50 μl each well into the 96-well plate inoculated with cells (double holes, final concentration of DMSO is 1%).
4. Dilution of virus: dilute EV71 virus solution by 10000 times to a concentration of 100TCID$_{50}$/50 μl. Add the diluted virus solution by 50 μl each well into the 96-well plate. Prepare another 96-well plate to replace the virus with culture medium and similarly inoculate the cells. Add the compound which is used to test the toxicity of compound on cells.
5. Cultivate the 96-well plate 3 days at the conditions of 37° C. and 5% CO$_2$.
6. EC50 and CC50 tests: add the cellular activity test reagent CCK8 into the micro-wells by 20 μl/well. Use ELIASA to read the absorbancy at the wavelength of 450 nm and 630 nm.
7. Analysis of data: analyze the data with Prism5.0 and calculate the antiviral activity of EC50 and the cellular toxicity of C50 of the compound.

The result is as shown in Table 5:

TABLE 5

Result of EC$_{50}$ by EC71 CPE test

| Test sample | EV71 |
|---|---|
| Compound 1 | ≤10 nM |

Conclusion: the compound 1 according to the present invention has an obvious inhibitory effect to EV71 virus at a cell level.

The invention claimed is:
1. A method for preparing compound 1,

Compound 1 comprising the following steps:

wherein,
molar ratio of the compound 3-2 and the NaNO$_2$ is between 1:1 and 1:2;
reaction solvent used in preparation of the compound 3-3 from the compound 3-2 is selected from methanol/water, ethanol/water, isopropanol/water or acetic acid/water;
volume ratio of the water and the methanol, the ethanol, the isopropanol or the acetic acid is between 1:1 and 1:3;
weight ratio of the compound 3-2 and H$_2$O is between 1:1 and 1:3.

2. The method according to claim 1, comprising the following steps:

wherein,
reaction solvent used in preparation of the compound 3-2 from the compound 3-1 is selected from methanol/dioxane, ethanol/dioxane, isopropanol/dioxane;
volume ratio of the dioxane and the methanol, the ethanol, or the isopropanol is 0.5 to 1:0.5 to 1;
molar ratio of the compound 3-1 and the alkali A is between 1:1 and 1:2;
the alkali A is selected from the group consisting of sodium methoxide, sodium ethoxide, potassium tert-butoxide, lithium tert-butoxide, sodium tert-butoxide, aluminium isopropoxide, sodium hydride, potassium hydride, calcium hydride, lithium hydroxide, sodium hydroxide, potassium hydroxide, cesium hydroxide, sodium carbonate, potassium carbonate, cesium carbonate, sodium hydrogen carbonate and potassium hydrogen carbonate;

molar ratio of the compound 3-1 and the hydrazine hydrate is between 1:2 and 1:15.

3. The method according to claim 1, comprising the following steps:

wherein,
molar ratio of the 2-amino-4-bromopyridine and the compound 2-4 is between 1:1 and 1:2;
molar ratio of the ligand and the compound 2-4 is between 0.1:1 and 0.5:1;
the ligand is selected from TRANS-N,N'-dimethylcyclohexyl-1,2-diamine, N,N'-dimethylethanediamine or Xphos;
the catalyst is selected from CuI, Pd$_2$(dba)$_3$;
molar ratio of the alkali B and the compound 2-4 is between 2:1 and 4:1;
the alkali B is selected from the group consisting of lithium hydroxide, sodium hydroxide, potassium hydroxide, cesium hydroxide, sodium carbonate, potassium carbonate, cesium carbonate, sodium hydrogen carbonate and potassium hydrogen carbonate;
reaction solvent used in preparation of the compound 2-5 from the compound 2-4 is selected from the group consisting of DMF, dioxane and dimethyl sulfoxide;
weight ratio of the reaction solvent and the compound 2-4 is between 10:1 and 20:1.

4. The method according to claim 1, comprising the following steps:

wherein,
the reductant is red-Al;
molar ratio of the compound 1-2 and the red-Al is between 1:1 and 1:4.

5. The method according to claim 1, comprising the following steps:

-continued compound 1

-continued compound 1

6. Compound 1 represented by the following formula and crystal form A thereof, XRPD spectrum of the crystal form A is as shown in FIG. 1:

Compound 1

7. Compound 2 represented by the following formula and crystal form B thereof, XRPD spectrum of the B form is as shown in FIG. 4:

compound 2

·HCl.

8. The method according to claim 2, comprising the following steps:

-continued